United States Patent
Dyell et al.

(10) Patent No.: US 11,205,513 B2
(45) Date of Patent: *Dec. 21, 2021

(54) REAL-TIME MONITORING SYSTEMS AND METHODS IN A HEALTHCARE ENVIRONMENT

(71) Applicant: VCCB Holdings, Inc., Wilmington, DE (US)

(72) Inventors: David Dyell, Panama City, FL (US); Christopher Rogowski, Newtown Square, PA (US); Scott Kahler, Tuscaloosa, AL (US); Jennifer Milan, Westminster, CO (US)

(73) Assignee: VCCB Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/061,853

(22) Filed: Oct. 2, 2020

(65) Prior Publication Data

US 2021/0166810 A1   Jun. 3, 2021

Related U.S. Application Data

(63) Continuation of application No. 16/730,775, filed on Dec. 30, 2019, now Pat. No. 10,827,928, which is a
(Continued)

(51) Int. Cl.
*G16H 40/67* (2018.01)
*A61B 5/00* (2006.01)
(Continued)

(52) U.S. Cl.
CPC ............ *G16H 40/67* (2018.01); *A61B 5/002* (2013.01); *A61B 5/0024* (2013.01); *A61B 5/02055* (2013.01); *A61B 5/486* (2013.01);

*A61B 5/746* (2013.01); *A61B 5/7475* (2013.01); *G16H 40/63* (2018.01); *G16H 50/20* (2018.01); *G16Z 99/00* (2019.02); *A61B 5/1112* (2013.01)

(58) Field of Classification Search
CPC combination set(s) only.
See application file for complete search history.

(56) References Cited

PUBLICATIONS

No 1449 forms nor any references have been submitted by the Applicants.*

* cited by examiner

*Primary Examiner* — Nabil H Syed
*Assistant Examiner* — Cal J Eustaquio
(74) *Attorney, Agent, or Firm* — Knobbe, Martens, Olson & Bear, LLP

(57) ABSTRACT

An apparatus for real time monitoring of a patient is provided and includes a memory element for storing data, a processor that executes instructions associated with the data, an interface that receives sensor data from a sensor that takes measurements from the patient and sends the sensor data according to the sensor's measurement latency, a latency calculator that frequently calculates a latency threshold that varies according to at least a health status of the patient, a timer that continuously monitors the sensor's measurement latency, a comparator that frequently compares the sensor's measurement latency with the calculated latency threshold, and a feedback module that automatically changes the sensor's measurement latency to match with the calculated latency threshold.

20 Claims, 6 Drawing Sheets

Related U.S. Application Data continuation of application No. 16/410,939, filed on May 13, 2019, now Pat. No. 10,517,480, which is a continuation of application No. 16/146,974, filed on Sep. 28, 2018, now Pat. No. 10,285,592, which is a continuation of application No. 14/835,709, filed on Aug. 26, 2015, now Pat. No. 10,111,591.

(60) Provisional application No. 62/042,110, filed on Aug. 26, 2014.

(51) Int. Cl.
*G16H 50/20* (2018.01)
*A61B 5/0205* (2006.01)
*G16Z 99/00* (2019.01)
*G16H 40/63* (2018.01)
*A61B 5/11* (2006.01)

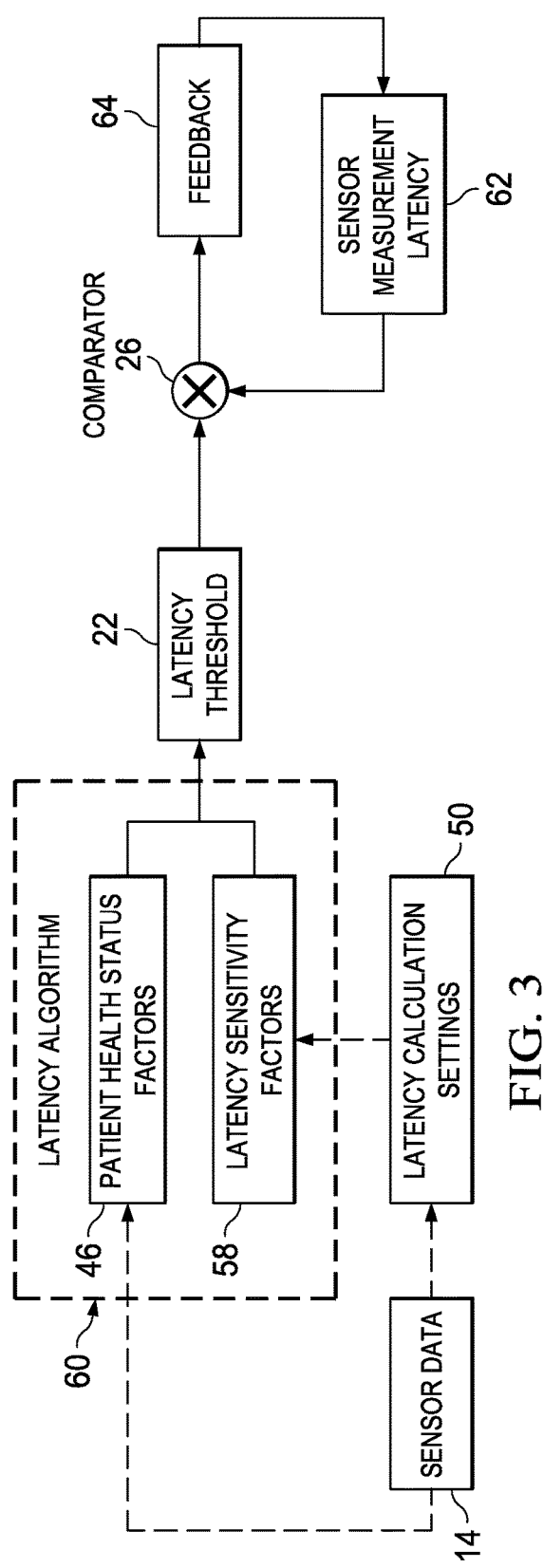
FIG. 3
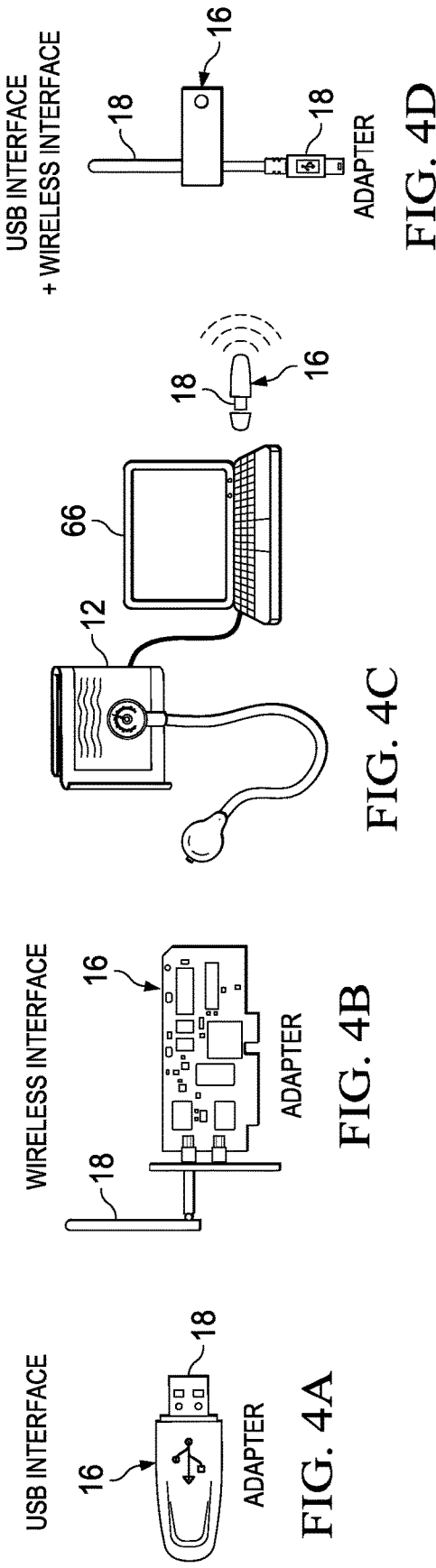
FIG. 4A
FIG. 4B
FIG. 4C
FIG. 4D

| SENSOR | VALUE | LATENCY | ALERT | CERTIFICATION |
|---|---|---|---|---|
| 1 | 30 | 4 SECONDS | GREEN | GOLD |
| 2 | 4.6 | 0 SECONDS | GREEN | GOLD |
| 3 | 16 | 20 SECONDS | YELLOW | SILVER |
| 4 | 80 | 4 MINUTES | RED | NONE |

REAL-TIME MONITORING SYSTEMS AND METHODS IN A HEALTHCARE ENVIRONMENT

CROSS-REFERENCE TO RELATED APPLICATION

This application is a continuation of U.S. patent application Ser. No. 16/730,775, filed on Dec. 30, 2019, entitled REAL-TIME MONITORING SYSTEMS AND METHODS IN A HEALTHCARE ENVIRONMENT, which is a continuation of U.S. patent application Ser. No. 16/410,939, filed on May 13, 2019, now issued as U.S. Pat. No. 10,517,480 on Dec. 31, 2019, and entitled REAL-TIME MONITORING SYSTEMS AND METHODS IN A HEALTHCARE ENVIRONMENT, which is a continuation of U.S. patent application Ser. No. 16/146,974, filed on Sep. 28, 2018, now issued as U.S. Pat. No. 10,285,592 on May 14, 2019, and entitled REAL-TIME MONITORING SYSTEMS AND METHODS IN A HEALTHCARE ENVIRONMENT, which is a continuation of U.S. patent application Ser. No. 14/835,709, filed on Aug. 26, 2015, now issued as U.S. Pat. No. 10,111,591 on Oct. 30, 2018, and entitled REAL-TIME MONITORING SYSTEMS AND METHODS IN A HEALTHCARE ENVIRONMENT, which relates to and claims the benefit of priority under 35 U.S.C. § 119(e) to U.S. Provisional Patent Application Ser. No. 62/042,110, filed on Aug. 26, 2014, and entitled REAL TIME MONITORING SYSTEMS AND METHODS, the disclosures of each of which are hereby incorporated by reference in their entirety.

TECHNICAL FIELD

This disclosure relates in general to the field of healthcare systems and, more particularly, to systems and methods related to real time monitoring in a healthcare environment.

BACKGROUND

The background description includes information that may be useful in understanding the present disclosure. It is not an admission that any of the information provided herein is prior art or relevant to the disclosure, or that any publication specifically or implicitly referenced is prior art.

Real-time monitoring of a patient or potential patient data can be crucial during times of a medical crisis. A difference of a few minutes or even seconds could mean the difference between life and death of the patient, or the difference between a brain-dead patient and a patient that is merely unconscious. As a result, a multitude of real-time monitoring sensors and systems have been developed to ensure that a patient's vitals are reported to appropriate entities in real-time.

For example, certain implantable medical devices periodically test a patient's vital stats to ensure that the current record of the patient's stats are always up to date. The medical device regularly polls the patient's stats at the same time every day. However, the system may over-test and over-report a patient's vital signs within time periods that are too short, wasting log space and possibly shortening the lifespan (i.e., loss of battery life) of the device by performing too many tests within an unnecessarily short period.

In another example, a monitoring sensor is implanted in the toilet of the patient. Whenever the patient urinates, the sensor tests the patient's urine to report the patient's vital information. Such a system, however, depends upon the patient's waste management schedule. If the patient doesn't need to eliminate waste, or uses a different toilet, extended periods of time may occur between testing cycles, making the reporting data unreliable.

In yet another example, a sensor system detects when a sensor is unable to report information, and during that interlude reports an estimated sensor value extrapolated from past sensor trend data. The estimated sensor value, however, may not be entirely accurate and violates the concept of real-time monitoring, since some vital information is not easily predicted using trends, especially during times of a medical emergency.

In yet another example, a sensor is embedded within a probe delivery device, ensuring that sensor data is created virtually as the probes are collected from the patient's body. Not all sensors, however, can be integrated into a patient's body to ensure that data is gathered so rapidly. Some sensors will inevitably have long periods of time in between collection periods.

In yet another example, a system collects sensor data at a rapid rate, ensuring that all data is at most 10 minutes old, and at times ensuring that all data is at most 0.1 seconds old. Again, some sensors may not be able to be configured to collect data at 0.1 second intervals, and there are some vital signs that don't need to be checked so often.

In yet another example, a real-time system monitors a patient in radiation therapy. The system refreshes the data collection in real-time (e.g., a time period that is not humanly discernible). Even if data collection is humanly discernible, however, some data need not be tested so many times in a row. Some vital signs could be tested every 0.1 second, while other vital stats could be checked every day or so.

Thus, there is still a need for systems and methods that ensure real-time data collection, which medical professionals could use to dictate when data is collected rapidly enough to be considered real-time for targeted intents or purposes.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

SUMMARY

An apparatus for real time monitoring of a patient is provided and includes a memory element for storing data, a processor that executes instructions associated with the data, an interface that receives sensor data from a sensor that takes measurements from the patient and sends the sensor data according to the sensor's measurement latency, a latency calculator that frequently calculates a latency threshold that varies according to at least a health status of the patient, a timer that continuously monitors the sensor's measurement latency, a comparator that frequently compares the sensor's measurement latency with the calculated latency threshold, and a feedback module that automatically changes the sensor's measurement latency to match with the calculated latency threshold. Thus, the disclosed system is able to adaptively or contextually determine the requirements or conditions for real-time monitoring of a patient or patient data.

As used herein, the term "latency" refers to a time delay determined at the apparatus between two consecutive measurements transmitted by the sensor. The sensor's measurement latency as determined at the apparatus can be influenced by (i) an inherent delay at the sensor between measuring a health parameter of the patient, processing it into transmittable sensor data, and transmitting the sensor data, and (ii) network latency inherent in a communication channel (e.g., wireless, Ethernet, optical fiber, etc.) between the apparatus and the sensor. For example, the sensor may measure a blood pressure of the patient; a digital signal processor at the sensor may convert analog readings of the blood pressure into digital data; a network interface card at the sensor may convert the digital data into network communication packets—a time delay may be inherent in these processes at the sensor. In addition, in some embodiments, the communication packets may be transmitted by the sensor across a wireless interface to the apparatus; the wireless medium may inherently add latency to the communication.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 3 is a simplified block diagram illustrating other example details of the system according to an embodiment;

FIG. 4A is a simplified block diagram illustrating yet other example details of the system according to an embodiment;

FIG. 4B is a simplified block diagram illustrating yet other example details of the system according to an embodiment;

FIG. 4C is a simplified block diagram illustrating yet other example details of the system according to an embodiment;

FIG. 4D is a simplified block diagram illustrating yet other example details of the system according to an embodiment;

DETAILED DESCRIPTION OF EXAMPLE EMBODIMENT

Figure 1:
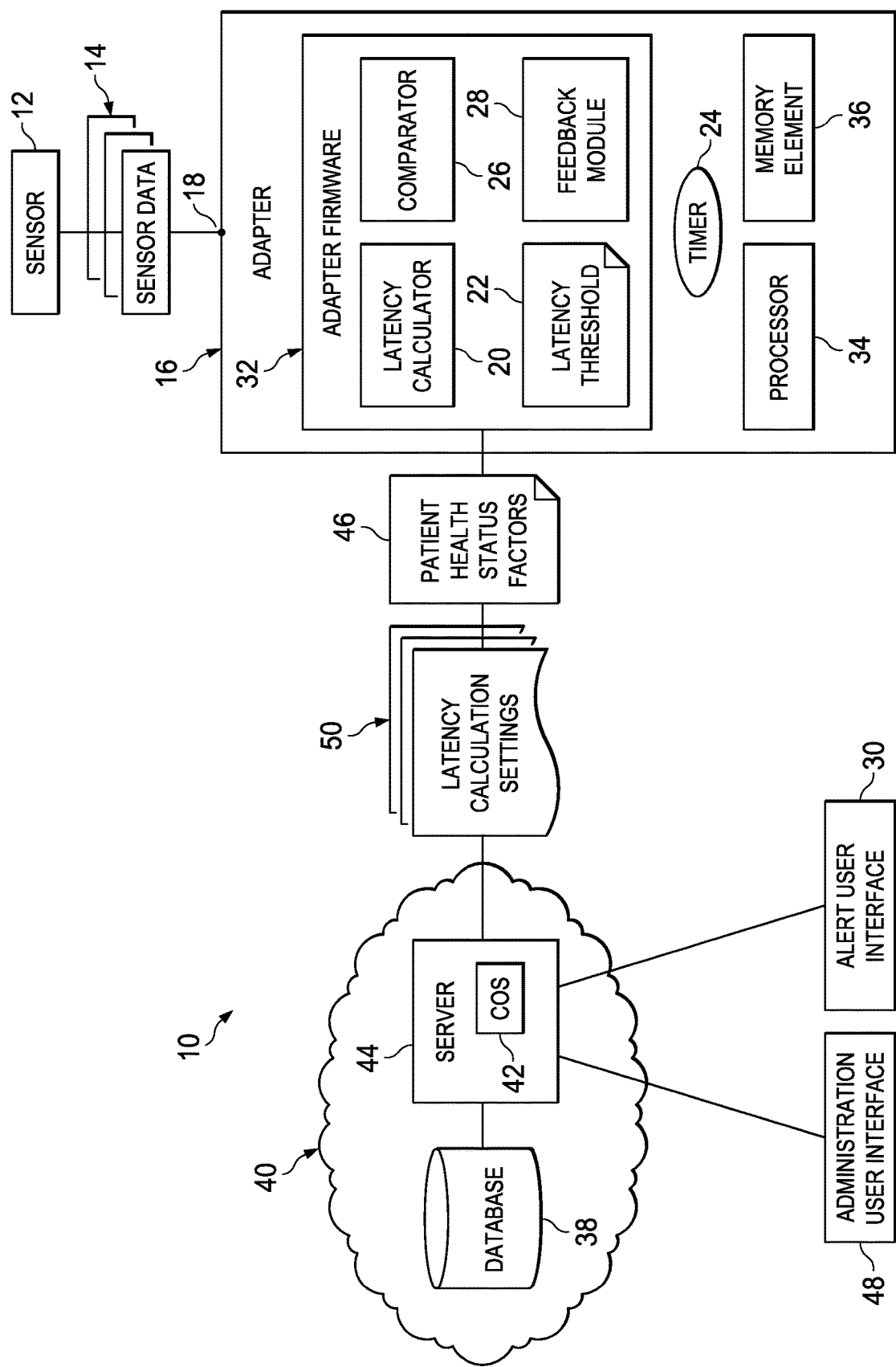
FIG. 1 is a simplified block diagram illustrating a system for real time monitoring according to an example embodiment.

Turning to FIG. 1, FIG. 1 is a simplified block diagram illustrating a system 10 according to an example embodiment. The disclosure herein provides apparatus, systems and methods in which a computer system is configured to examine information collected by sensors monitoring a patient and determine whether the sensor data is collected rapidly enough to be considered "real-time" information. A sensor 12 monitors a patient (not shown), and generates sensor data 14 comprising measurements of one or more health parameters of the patient. Examples of sensor 12 include global positioning system (GPS) locators, pulse and blood pressure monitors, pulse oximeters, galvanometers, blood glucose monitors, body temperature monitors, and catheter monitors. By way of examples, and not as limitations, sensor data 14 can include location information, pulse information, blood pressure information, blood chemical concentration level information, body temperature information, respiration level information, and fluid level information. Sensors 12 could be configured to be attached or implanted into the patient, or could be located within the vicinity of the patient, such as a room that the patient uses on a regular basis.

Sensor 12 transmits sensor data 14 to an adapter 16 according to a measurement latency of sensor 12; adapter 16 receives sensor data 14 over an interface 18. Sensor data 14 may be transmitted via any suitable communication medium in different embodiments, for example using wired (e.g., RS-232, Ethernet, USB, etc.) or wireless signals (e.g., WUSB, Bluetooth®, WiFi, WiGIG, WiMAX, etc.) received by a transmitter, printouts read by a scanner, tissue or bodily fluid samples tested by a lab, or information input from a nurse or doctor into the system using a computer user interface. In some embodiments, one or more interfaces are typically used as a bridge to help transmit sensor data 14 from sensor(s) 12 to one or more computer systems.

In a general sense, because information collection systems inherently have a delay, adapter 16 includes a latency calculator 20 that determines how much of a delay is acceptable to be considered information that has been collected in 'real time.' The threshold for this delay is referred to herein as "latency threshold" 22 possibly with respect to a targeted intent or purpose. Latency calculator 20 frequently calculates latency threshold 22 for sensor data 14. A timer 24 monitors time of receipt of sensor data 14 at adapter 16 and thereby substantially continuously monitors sensor 12's measurement latency. In some embodiments, timer 24 monitors sensor 12's measurement latency based in two consecutive receipts of sensor data 14, among multiple measurements (e.g., rolling average over N difference measurements, etc.), based on slopes of measurement rates, or other factors. In an example embodiment, timer 24 monitors frequency of incoming sensor data 14 (e.g., in the form of sensor pulses) from sensor 12. In a general sense, latency threshold 22 indicates a threshold or criterion, where any measurement latency at or above latency threshold 22 (or otherwise fails to satisfies the criteria), is considered unacceptable and any measurement latency below latency threshold 22 (or otherwise satisfies the criteria), is considered acceptable. Measurement latency and latency threshold 22 could be defined in units of time, such as microseconds, milliseconds, seconds, minutes, or hours. A comparator 26 frequently compares the sensor's measurement latency with calculated latency threshold 22. Sensor data 14 that is received at adapter 16 within latency threshold 22 could be considered "real-time" information, whereas sensor data 14 that is received at adapter 16 after latency threshold 22 has lapsed could be considered "retrospective" information.

A feedback module 28 may provide feedback according to the comparison at comparator 26. For example, if sensor data 14 is retrospective information, feedback module 28 may automatically change sensor 12's measurement latency to match with calculated latency threshold 22. In another example embodiment, if sensor data 14 is retrospective information, feedback module 28 may generate an alert at an alert user interface 30. Various other feedback actions may be facilitated according to the broad scope of the embodiments.

In various embodiments, adapter 16 may be provisioned with firmware 32 that can provide various functionalities as described herein. In one example embodiment, firmware 32 includes an application specific integrated circuit (ASIC) programmed with latency calculator 20, comparator 26, and feedback module 28 with associated memory for storing calculated latency threshold 22. A processor 34 may provide processing functionalities not included in firmware 32. A memory element 36 may comprise various memory storage functions of adapter 16. In another example embodiment, firmware 32 may comprise a volatile memory that includes instructions for executing functionalities of latency calculator 20, comparator 26, and feedback module 28 with associated memory for storing calculated latency threshold 22. Processor 34 may execute the instructions from firmware 32 appropriately. In an example embodiment, adapter 16 may comprise or be an integral part of, the Nant Health, LLC, HBox® device. In some embodiments, adapter 16 could include one or more computer systems operating according to the Nant Health, LLC, DeviceConX™ software platform.

In various embodiments, adapter 16 may communicate with a database 38 over a network 40 through a clinical operating system (cOS™) 42, possibly offered by Nant Health, LLC (see URL nanthealth.com/cos-clinical-operating-system). In various embodiments, cOS 42 executes on a server 44 in network 40 remote from adapter 16. Example suitable cOS 42 that can be suitably adapted for use with the disclosed subject matter includes those described by U.S. Pat. No. 8,689,008, and U.S. pre-grant publications 2011/0313787, 2013/0054272, 2013/0144653, 2013/0166317, 2013/0304512, and 2013/0304496, the disclosures of which are incorporated herein in their entireties. Database 38 may provide various patient health status factors 46, using which latency calculator 20 at adapter 16 can determine latency threshold 22. In various embodiments, the patient health status comprises a data construct of an aggregate of health conditions, population characteristics, diseases, symptoms, medications and medical status of the patient, indicative of a context of measurements by sensor 12. An administration user interface 48 may interface with adapter 16 through cOS 42 to provide various latency calculation settings 50.

In various embodiments, patient health status factors 46 may include various parameters and corresponding values that influence latency threshold 22. By way of examples, and not as limitations, patient health status factors 46 include patient location, patient disease or health condition (e.g., diabetes, heart disease, etc. for example, formatted as International Statistical Classification of Diseases and Related Health Problems (ICD-9 codes)), physician location, clinical pathways associated with the patient, patient's treatment regimen, genomic health indicators, demographic information and contextual information relevant to sensor data 14 (e.g., patient in emergency room following cardiac arrest; patient checking fasting blood sugar at home according to daily health regimen; patient on a regular exercise walk; patient in maternity ward about to have a C-section; etc.). Virtually any suitable parameter that affects a health status of the patient could be included in patient health status factors 46.

In various embodiments, latency calculation settings 50 may provide variables, values, or algorithms for calculating latency threshold 22. In one example embodiment, latency calculations settings 50 may indicate that latency threshold 22 be calculated as a function of one or more of patient health status factors 46 and a type of the sensor data 14 being collected. For example, latency threshold 22 of blood sugar measurement for a patient without diabetes may be 30 minutes, whereas latency threshold 22 of blood sugar measurement for another patient with diabetes may be 10 minutes. In another example, latency threshold 22 of blood pressure measurement for a patient at a trauma center may be 5 minutes, whereas latency threshold 22 of blood pressure measurement for a patient monitoring her general health at her home may be 1 week.

In some embodiments, latency calculation settings 50 may indicate several latency thresholds for sensor 12, allowing for granulated feedback (e.g., alerts). For example, a heartbeat sensor could be associated with a 'yellow' latency threshold of 10 seconds, an 'orange' latency threshold of 30 seconds, and a 'red' latency threshold of 1 minute, where the color indicates a level of urgency or importance.

In some embodiments, latency calculation settings 50 may indicate contextual information (e.g., time, location, area congestion, demographic, genomic information, health trends, user preferences, etc.) for latency threshold calculations. For example, latency threshold 22 for a patient next to a sports stadium may be lower than latency threshold 22 for the patient next to a freeway entrance. In another example, latency threshold 22 for a patient in the urgent care wing of a hospital may be higher than latency threshold 22 for the patient in an outpatient area. In some embodiments, latency calculation settings 50 may indicate that latency calculator 22 take into consideration the location of the patient relative to a nearest healthcare provider. For example, latency threshold 22 for a patient located 5 minutes away from the nearest acceptable doctor may be higher than latency threshold 22 for another patient located 30 minutes away from the nearest acceptable doctor.

In some embodiments, adapter 16 may interface with more than one sensor 12. In such embodiments, latency calculation settings 50 may indicate that latency calculator 20 take into consideration the type of sensor data 14. For example, blood sugar measurement latency threshold may be higher than pulse measurement latency threshold. In another example, latency calculation settings 50 may indicate a dependence of latency threshold for one sensor on latency threshold for another sensor. For example, where sensor data from a first sensor affects sensor data from a second sensor, latency threshold 22 for the first sensor may be lower than latency threshold 22 for the second sensor.

In some embodiments, latency calculation settings 50 may configure latency calculator 20 to add or subtract a buffer latency to calculated latency threshold 22. The buffer latency could be associated with the patient and be stored as part of the patient's health status in database 38 in some embodiments. In other embodiments, buffer latency could be associated with a healthcare provider or location and provided to adapter 16 as part of latency calculation settings 50. Buffer latency may be provided in some embodiments where adapter 16 does not have sufficient processing capabilities to compute buffer latency based on network settings and other variables.

In some embodiments, a user, such as a doctor or other healthcare professional, can tweak one or more latency calculation settings 50, including buffer latency, through administration user interface 48. In some embodiments, administration user interface 48 may provide a selectable menu from which the user can select a set of pre-defined functions for each sensor type, and to modify such functions for a patient or type of patient. The functions, including modifications thereof, may be included in latency calculation settings 50 and can be used to configure (e.g., program, update, etc.) adapter 16.

In some embodiments, feedback module 28 triggers an alert when measurement latency of sensor 12 as measured by frequency of incoming sensor data 14 exceeds calculated latency threshold 22. Any suitable alert mechanism could be used, for example sending a page to a healthcare provider or displaying an indicator, such as a red light, on a user interface. Such alerts could be transmitted in audio, visual, or tactile form in locations proximal to a patient to locations very far away from the patient. In some embodiments, alert user interface 30 may be used to allow the user to configure the type of alert, although pre-defined alerts could be programmed into system 10. For example, if the sensor's measurement latency falls above latency threshold 22, system 10 could be configured to automatically derive the nearest healthcare provider and send an alert to that healthcare provider. Feedback module 28 could also trigger an alert when two sensors that should be reporting in-sync are out of sync with one another. For example, feedback module 28 might be programmed to ensure that the collection periods of two different sensors are within 20 seconds of one another, where a first sensor always collects information prior to a second sensor collecting information.

One should appreciate that the disclosed techniques provide many advantageous technical effects including allowing a plurality of definitions for what is considered "real time," which may be dependent upon a particular patient's health status instead of on a global number applied universally to all patients. Thus, the definition of "real time" directly impacts the functionality of the devices disclosed herein to ensure the definition is enforced.

Turning to the infrastructure of system 10, the network topology of network 40, including the network connecting to adapter 16 and/or sensor 12 can include any number of servers, routers, gateways, and other nodes inter-connected to form a large and complex network. A node may be any electronic device, client, server, peer, service, application, or other object capable of sending, receiving, or forwarding information over communications channels in a network. Elements of FIG. 1 may be coupled to one another through one or more interfaces employing any suitable connection (wired or wireless), which provides a viable pathway for electronic communications. Additionally, any one or more of these elements may be combined or removed from the architecture based on particular configuration needs.

System 10 may include a configuration capable of Transmission Control Protocol/Internet Protocol (TCP/IP) communications for the electronic transmission or reception of data packets in a network. Healthcare monitoring system 10 may also operate in conjunction with a User Datagram Protocol/Internet Protocol (UDP/IP) or any other suitable protocol, where appropriate and based on particular needs. In addition, gateways, routers, switches, and any other suitable nodes (physical or virtual) may be used to facilitate electronic communication between various nodes in the network.

Note that the numerical and letter designations assigned to the elements of FIG. 1 do not connote any type of hierarchy; the designations are arbitrary and have been used for purposes of teaching only. Such designations should not be construed in any way to limit their capabilities, functionalities, or applications in the potential environments that may benefit from the features of healthcare monitoring system 10. It should be understood that system 10 shown in FIG. 1 is simplified for ease of illustration.

The example network environment may be configured over a physical infrastructure that may include one or more networks and, further, may be configured in any form including, but not limited to, local area networks (LANs), wireless local area networks (WLANs), virtual local area networks (VLANs), metropolitan area networks (MANs), wide area networks (WANs), virtual private networks (VPNs), Intranet, Extranet, any other appropriate architecture or system, or any combination thereof that facilitates communications in a network.

In some embodiments, a communication link may represent any electronic link supporting a LAN environment such as, for example, cable, Ethernet, wireless technologies (e.g., IEEE 802.11x), ATM, fiber optics, etc. or any suitable combination thereof. In other embodiments, communication links may represent a remote connection through any appropriate medium (e.g., digital subscriber lines (DSL), telephone lines, T1 lines, T3 lines, wireless, satellite, fiber optics, cable, Ethernet, etc. or any combination thereof) and/or through any additional networks such as a wide area networks (e.g., the Internet).

In various embodiments, adapter 16 can include computer executable instructions stored on one or more non-transitory computer-readable media (e.g. adapter firmware 32, including hard drives, optical storage media, flash drives, ROM, RAM, etc.) that, when executed by one or more processors (e.g., processor 34), cause the processors to execute the functions and processes described herein. In some embodiments, some functionalities of adapter 16 may be implemented in a distributed manner, for example, at server 44 (through cOS 42). In some embodiments, adapter 16 may be generally compatible with any type of sensor, but may be specifically configured to calculate latency threshold 22 for the specific type of sensor data 14 from sensor 12 with which it interfaces. In other embodiments, adapter 16 may be configured to be compatible with only one type of sensor 12, for example, with different adapters for different sensor types. Example devices that may be suitable for adaption according to the disclosed techniques include device server product offerings from Lantronix®, Digi®, or Moxa®. For example, the Digi One SP or the wireless (e.g., 802.11b) Digi Connect Wi-SP device servers can be configured with firmware according to the disclosed techniques.

In various embodiments, cOS 42 may include a suitable operating system (or platform, or other appropriate software) that can federate various disparate data (e.g., from health providers, patients, sensors, other medical devices, etc.), aggregate the data in disparate formats to a uniform format (e.g., JSON, YAML, XML based format), and store the uniformly formatted data in a suitable data store (e.g., federated centralized database; data store for aggregated data) such as database 38 in network 40. cOS 42 may comprise a plurality of self-contained interconnected modules and service layers for connecting proprietary (and public) systems together and extracting and translating data therefrom to enable them to cooperate in a software ecosystem while allowing flexible connections with both existing and new applications. cOS 42 may offer a secure communication tunnel for adapter 16 to interface with database 38, administration user interface 48 and alert user interface 30. In some embodiments, cOS 42 can generally allow adapter 16 to interface with various other computer systems and/or adapters in network 40.

Figure 2:
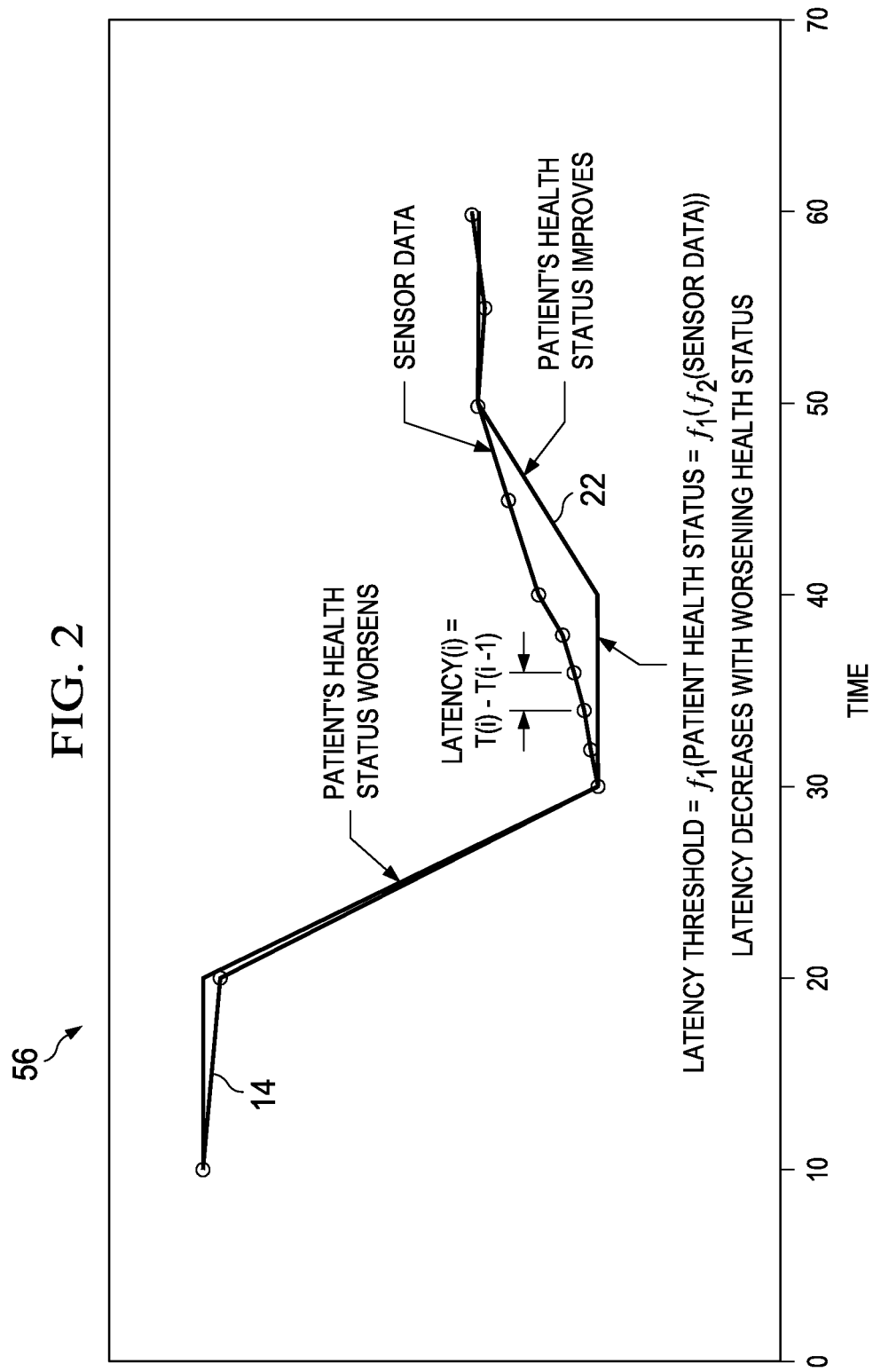
FIG. 2 is a simplified diagram illustrating example details of the system according to an embodiment.

Turning to FIG. 2, FIG. 2 is a simplified diagram illustrating example details according to an embodiment of system 10. A hypothetical graph 56 shows sensor data 14 plotted against time on the X-axis. Sensor 12's measurement latency at time i can be derived as latency(i)=T(i)−T(i−1); in other words, the latency at any instant of time is the time difference (e.g., time delay) between the time at measurement i and the previous time at measurement (i−1). Assume that the patient has stable health status initially. Latency threshold 22 for the initial measurements may be 10 minutes. Thus, sensor 12 may measure the patient every 10 minutes. Assume that between the measurement at 20 minutes and the next measurement at 30 minutes, the patient suffers a worsening health condition (e.g., blood sugar rises uncontrollably, blood sugar drops precariously, etc.), as indicated by sensor data 14.

In some embodiments, sensor data 14 may be communicated to database 38, which may process sensor data 14, convert into one or more patient health status factors 46 and transmit to adapter 16. In other embodiments, adapter 16 may use sensor data 14 directly to calculate latency threshold 22. Latency calculator 20 may recalculate latency threshold 22 to be 2 minutes, rather than 10 minutes, based on the changing patient's health status. Comparator 26 may compare sensor 12's measurement latency of 10 minutes with latency threshold 22 of 2 minutes and identify a discrepancy. Feedback module 28 may alter measurement latency of sensor 12 to match with latency threshold 22 Sensor 12 may thereafter measure the patient every 2 minutes. Thus, it should be appreciated that latency threshold 22 adapts to the patient context or health status context.

Assume that sensor data 14 (and/or other parameters) indicates that the patient's health status improves at 40 minutes. Latency calculator 20 may recalculate latency threshold 22 to be 5 minutes, rather than 2 minutes, based on the changing patient's health status. Comparator 26 may compare sensor 12's measurement latency of 2 minutes with latency threshold 22 of 5 minutes and identify a discrepancy. Feedback module 28 may alter measurement latency of sensor 12 to match with latency threshold 22. Sensor 12 may thereafter measure the patient every 5 minutes. Thus, latency threshold 22 may be calculated to be a function of the patient health status (e.g., latency threshold=$f_1$(patient health status), which in turn may be a function of sensor data (e.g., patient health status=$f_2$(sensor data); latency threshold=$f_1(f_2$(sensor data))). In various embodiments, measurement latency of sensor 12 may decrease with worsening health status, and increase with improving health status. In other words, the concept of real-time monitoring may change depending on the patient's health status.

Turning to FIG. 3, FIG. 3 is a simplified block diagram illustrating example details according to an embodiment of system 10. Sensor data 14 may influence (e.g., affect, change, determine, etc.) patient health status factors 46. In some embodiments, sensor data 14 may affect latency calculation settings 50. For example, sensor data 14 of blood sugar of a patient who has hitherto not had a diagnosis of diabetes indicates onset of diabetes; thereafter latency calculation settings 50 may be changed to include a location of the nearest dialysis center. Sensor data 14 may affect patient health status factors 46; for example, a suddenly low blood sugar reading may indicate hypoglycemia.

In some embodiments, latency threshold 22 varies according to latency sensitivity factors 58. In an example embodiment, latency sensitivity factors 58 can include a subset of latency calculation settings 50. For example, latency calculation settings 50 may include location of dialysis center=2 miles from patient location; location of nearest emergency center=5 miles from patient location; latency threshold for heart patient=2 seconds for blood oxygen level readings; etc. Latency sensitivity factors 58 for latency threshold 22 for a blood sugar monitor sensor 12 may derive therefrom various factors that affect blood sugar readings and/or latency thresholds thereof, while ignoring settings of factors that do not affect blood sugar readings and/or latency thresholds thereof. In another example, latency sensitivity factors 58 may include functions that affect latency threshold calculations; for example, latency sensitivity factors 58 may include a linear function of latency threshold 22 with blood sugar readings; the actual blood sugar readings may be obtained from sensor data 14.

Patient health status factors 46 and latency sensitivity factors 58 may be input into an implementation of a latency algorithm 60 that outputs latency threshold 22. In some embodiments, latency algorithm 60 may be pre-configured into adapter 16. In other embodiments, latency algorithm 60 may be pre-selected by a user and used to configure latency calculator 20 in adapter 16. Comparator 26 may compare sensor 12's measurement latency 62 with calculated latency threshold 22 and generate a feedback 64 that may be used to change sensor's measurement latency 62 to match with latency threshold 22. Some embodiments include a rules interface (e.g., GUI, user interface, API, etc.) through which a stakeholder is able to define or implement rules logic for latency algorithm 60. For example, a stakeholder could download a script (e.g., Python, Lua, Java, C #, etc.) to adapter 16 where the script defines the operations necessary to calculate latency threshold 22 based on contextual data, internal or external, available to adapter 16.

Turning to FIGS. 4A-4D, FIGS. 4A-4D are simplified block diagrams illustrating example details of interfaces according to embodiments of system 10. In one example embodiment, as indicated by FIG. 4A, adapter 16 may be coupled to sensor 12 over a Universal Serial Bus (USB) interface 18. In another example embodiment, as indicated by FIG. 4B, adapter 16 may be integrated with sensor 12 and communicate with cOS 42 over a wireless interface 18. In another example embodiment, as indicated by FIG. 4B, adapter 16 may be integrated with a computing device or network element (e.g., switch) and communicate with sensor 12 over wireless interface 18. In yet another example embodiment, as indicated by FIG. 4C, adapter 16 may comprise a wireless component that is connected to a computer 66 over a USB interface and communicate with sensor 12 over a wireless interface 18. In some embodiments, computer 66 may communicate with (or be attached to) sensor 12, and adapter 16 may communicate with sensor 12 directly through computer 66. In yet another embodiment, as indicated by FIG. 4D, adapter 16 may include a wired (e.g., USB) interface 18 and another wireless interface 18. Various different types of interfaces 18 may be used within the broad scope of the embodiments.

Figure 5:
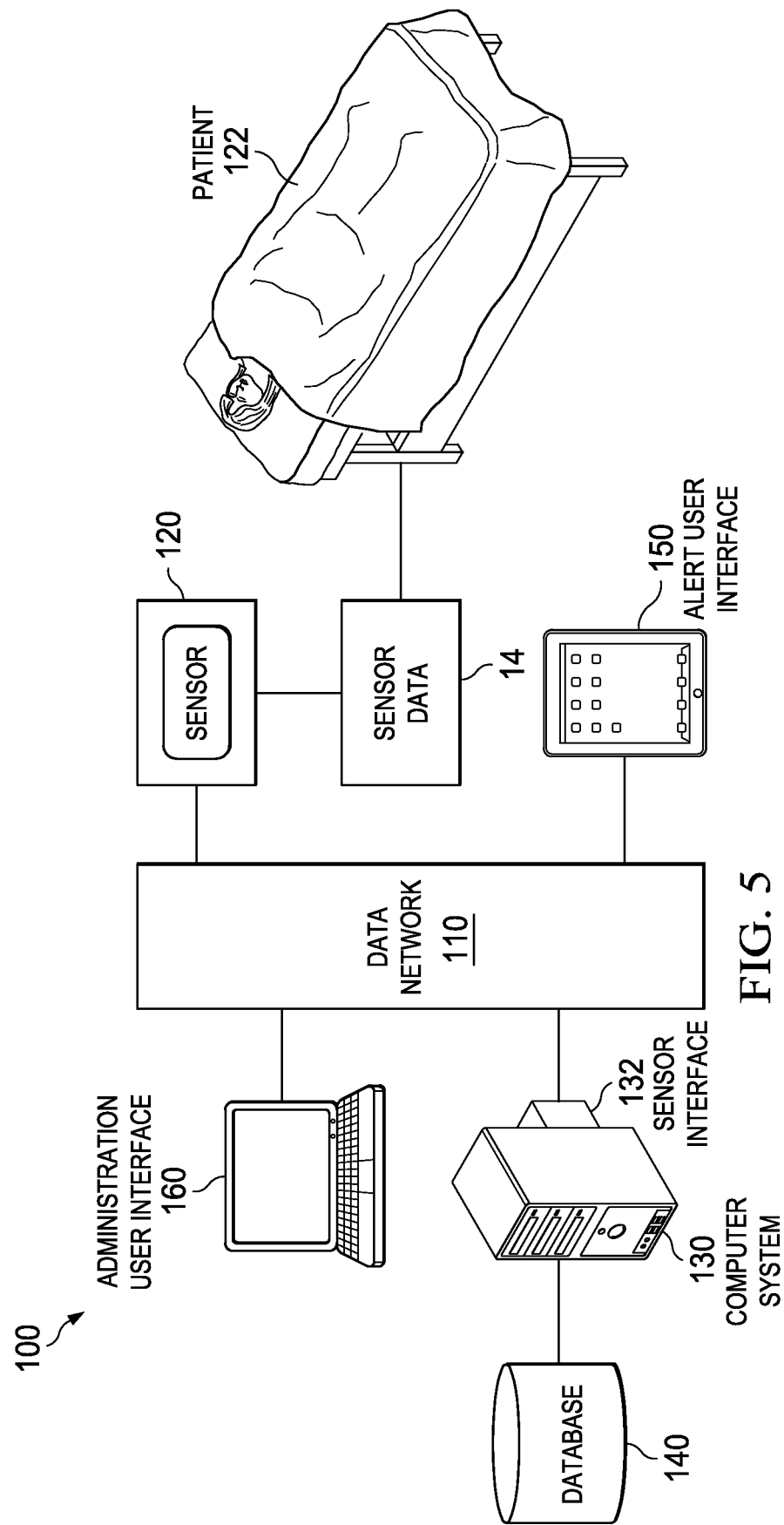
FIG. 5 is a simplified block diagram illustrating yet other example details of the system according to an embodiment.

Turning to FIG. 5, FIG. 5 is a simplified block diagram illustrating example details of an embodiment of system 100. The example hardware schematic indicates a data network 110, a sensor 120 monitoring a patient 122, a computer system 130, a database 140, an alert user interface 150, and an administration user interface 160. Data network 110 functionally connects various computing devices with one another such that data can flow from one device to another. Data network 110 comprises a package-switched network, a LAN, a WAN, a VPN, an intranet, an internet, or the Internet network. Data network 110 could comprise any suitable wired or wireless network known in the art using known protocols.

Sensor 120 gleans sensor data 14 from patient 122, and transmits sensor data 14 through data network 110 to computer system 130 through a sensor interface 132. In various embodiments, sensor interface 132 may comprise Bluetooth™ connection, WiFi connection, Ethernet connection, serial port, or other electronic data connection. Sensor 120 could comprise any suitable measuring device that monitors patient 122 and transmits sensor data 14 over data network 110 to computer system 130. In example embodiments, sensor 120 may include GPS/WiFi/RFID locators, pulse and blood pressure monitors, blood glucose monitors, body temperature monitors, and catheter monitors. In various embodiments, sensor data 14 includes location information, pulse information, blood pressure information, blood chemical concentration level information, body temperature information, respiration level information, and fluid level information. Sensor 120 may be configured to be attached or implanted into patient 122, or could be located within a room that patient 122 uses on a regular basis.

Sensor data 14 transmitted to computer system 130 via sensor interface 132 may be processed by computer system 130 to determine a health status of patient 122, and to determine whether sensor data 14 is in real-time. Computer system 130 has access to database 140, which may comprise a non-transient computer-readable memory storage device that generally holds relevant information used by computer system 130, such as software to perform system functions, health data about one or more patients, including patient 122, configuration data regarding latency thresholds, locations of healthcare providers, abilities of healthcare providers, and other medically relevant data. Computer system 130 automatically calculates latency threshold 22 for sensor 120 based upon the type of sensor data 14 received and the health status of patient 122, monitors incoming sensor data 14 from sensor 120, and sends an alert to one or more alert locations if sensor's measurement latency 62 data exceeds the calculated latency threshold 22. Alert user interface 150 comprises one such alert location that computer system 130 sends a triggered alert to. While alert user interface 150 is shown as a portable user interface functionally coupled to data network 110, alert user interface 150 could be sent the alert through other communication means without departing from the scope of the disclosure.

An administration user interface 160 can configure, update, and glean information from computer system 130 through data network 110. While computer system 130 generally has a table (e.g., a look-up table) of formulas that are applied to different sensors and to patients of various health statuses, administration user interface 160 could be used to customize a calculated formula for specific patient 122, or a group of patients, and/or could be used to add or subtract a buffer latency to the calculated formula. Administration user interface 160 could also be used to update information on any health status of patient 122, or could be used to monitor the real-time status of a plurality of sensors that are collecting information from patient 122.

Figure 6:
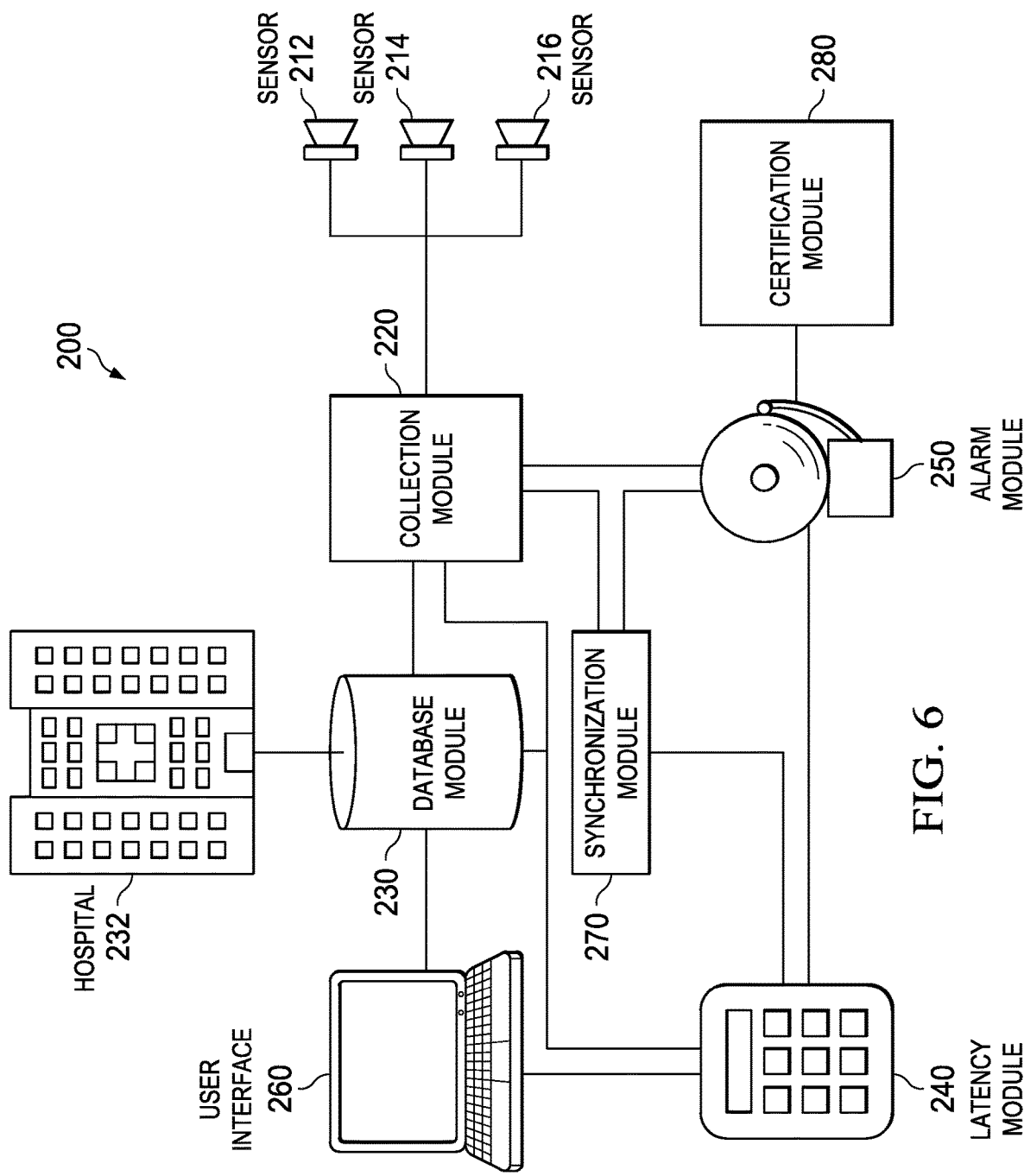
FIG. 6 is a simplified block diagram illustrating yet other example details of the system according to an embodiment.

Turning to FIG. 6, FIG. 6 is a simplified block diagram illustrating an example real-time monitoring system 200. System 200 comprises sensors 212, 214, and 216, collection module 220, database module 230, latency module 240, alarm module 250, user interface 260, synchronization module 270, and a certification module 280. Sensors 212, 214, and 216 monitor a patient (not shown) and are configured to send respective sensor data to collection module 220 in any suitable manner. For example, sensors 212, 214, and 216 could be configured to send information to collection module 220 according to a timer, collection module 220 could be configured to instruct sensors 212, 214, and 216 to send data after a certain time period has passed, or collection module 220 could be configured to regularly send requests to sensors 212, 214, and 216 in accordance with a schedule. Collection module 220 generally sends the collected sensor data to database module 230 to update the patient's health status, to latency module 240 to help determine whether the sensor data is in real-time, and to alarm module 250 to help determine whether an alert needs to be triggered.

In some embodiments, collection module 220 could be configured to receive or retrieve sensor data from one or more sensors 212, 214, 216 via respective sensor interfaces. In some embodiments, collection module 220 could be in active mode, configured to send requests for information from sensors 212, 214, 216 at pre-defined intervals. In other embodiments, collection module 220 could be in passive mode, collecting sensor data 14 from sensors 212, 214, 216 that actively send sensor data 14 regularly at pre-defined intervals. In some embodiments, collection module 220 can configure sensors 212, 214, 216, for example configuring a collection time period, measurement latency, or collection sample size.

User interface 260 may be used to allow a user to administer to system 200. For example, user interface 260 could be used to review and update the health status of a patient, to review any triggered alerts, to diagnose and update the collection periods of any of sensors 212, 214, or 216, to review and update any algorithms or tables used to calculate latency threshold 22, or to define a certification schema. In some embodiments, system 200 may be configured with predefined templates to monitor sensors 212, 214 and 216 and trigger alerts without any user definitions, but could be configured to allow a user to modify or redefine algorithms and data used by system 200 without departing from the scope of the embodiments.

Database module 230 gleans, stores, and organizes information regarding the health status of the patient, such as the patient's location, designated health care providers (e.g., designated hospitals, insurance carriers, medical professionals, etc.), illnesses, medication, allergies, types of sensors monitoring the patient, sensor history, medical history, and responsible party contact information. The health status of the patient could be gleaned from a variety of sources, for example from computerized patient records, from a user interface through which a health professional inputs data, from past sensor data, or from hospital 232. In some embodiments, database module 230 may be coupled to a portion of non-transient computer readable memory (e.g., RAM, FLASH, SAN, NAS, HDD, SSD, RAID, etc.) that is dedicated towards organizing and saving patient information. The data stored by database module 230 could be gleaned from sensor data 14 collected by collection module 220.

Latency module 240 calculates latency threshold 22 for each of sensors 212, 214, and 216. In some embodiments, latency module 240 could be configured to configure a plurality of acceptable sensor measurement latencies for each sensor 212, 214, and 216, for example a first sensor measurement latency that would trigger a yellow alert warning and a second sensor measurement latency that would trigger a red alert warning. In an example embodiment, latency threshold 22 may be derived as function of at least the type of sensor data 14 and the health status of the patient. A latency table could be used by latency module 240 to determine latency threshold 22, where one axis of the table is the type of sensor data 14 and the other axis of the table is the health status of the patient. Such a latency table could be multi-dimensional to consider other factors, such as the location of the patient, the location of the patient relative to the nearest healthcare provider, or sensor data from other sensors.

In other embodiments, numerical algorithms, such as latency algorithm 60 could be used to derive the latency threshold for a particular patient. An example numerical algorithm could comprise L=T*S−D, where L=sensor measurement latency, T=the type of sensor, S=health status, and D=distance from nearest healthcare provider (assuming normalized units). Thus, a type of sensor having a 2 minute standard delay, monitoring the health status of a patient having a health status of severity 2 that is 30 seconds from the nearest healthcare provider could have a sensor measurement latency of 2*2−0.5=3.5 minute sensor measurement latency. On the other hand, a type of sensor having a 1 minute standard delay monitoring the health status of a patient having a health status of severity 1 that is 45 seconds from the nearest healthcare provider could have a sensor measurement latency of 1*1−0.75=0.25 minute, or 15 second, sensor measurement latency. Other suitable algorithms to calculate latency threshold 22 could be used without departing from the scope of the embodiments.

Alarm module 250 triggers an alarm based upon the calculated latency threshold 22 derived by latency module 240 and the actual sensor measurement latency gleaned by collection module 220. If the sensor measurement latency of any of sensors 212, 214, and 216 rises above the calculated latency threshold 22, alarm 250 triggers an alarm, which may be sent to an authorized healthcare provider. Such alarms could be sent through any suitable means, for example though an email, text message, phone call, indicator light on a remote user interface, or audio sound.

In various embodiments, synchronization module 270 may be configured such that when an alert associated with one of sensors 212, 214 and 216 is triggered by alarm module 250, synchronization module 270 automatically seeks to redefine the collection time period of sensor 212, 214 or 216 in question to prevent such alerts from occurring in the future. For example, synchronization module 270 could be configured to have collection module 220 instruct sensor 212, 214 or 216 in question to have a shorter collection time period within the bounds of calculated latency threshold 22, or synchronization module 270 could arrange to have a page sent to a technician, instructing that technician to manually redefine the time period of sensor 212, 214 or 216 in question, or perhaps replace affected sensor 212, 214 or 216. In some embodiments, for example, wherein latency threshold 22 is dependent upon another sensor (i.e. data from sensor 214 needs to be received within 1 minute of data from sensor 212) synchronization module 270 is configured to modify the collection time period of a plurality of sensors in response to a single triggered alert.

In some embodiments, synchronization module 270 may be coupled to alarm module 250 and collection module 220, such that when an alert is triggered, synchronization module 270 automatically sends a command to collection module 220 to reduce the measurement latencies (e.g., time between collection periods) to an acceptable level (e.g., matching with latency threshold 22). Where two or more sensors 212, 214 or 216 are to be synched with one another, synchronization module 270 may be configured to alter the measurement latency of one or more sensors 212, 214 or 216 as a function of the latency threshold and measurement latency of another one of sensors 212, 214 or 216. In some embodiments, synchronization module 270 can be further configured, for example in a distributed healthcare collection environment, to create a point-of-collection agent within one or more computing devices. The point-of-collection represents a node where sensor data 14 can be collected together from plurality of sensors 212, 214 and 216 in a mutually contemporaneous manner, at least to within latency threshold 22. The point-of-collection agent can bundle collected sensor data 14 as a sensor event packet and send it to an analysis module. Thus, system 10 can be assured that the sensor event packet represents a proper sensor snap shot in time.

Certification module 280 is configured to monitor alerts triggered by alert module 250, and to issue a certification when an alert is not triggered for a threshold amount of time. A plurality of different types of certifications could be handled by certification module 280. For example, a certification could be issued when a single sensor 212, 214 or 216 has not triggered an alert for a threshold period of time, a certification could be issued when all sensors 212, 214 and 216 monitoring a particular patient have not triggered an alert for a threshold period of time, or a certification could be issued when all sensors 212, 214 or 216 monitoring all patients have not triggered an alert for a threshold period of time. A plurality of threshold periods of time could be defined for a plurality of certifications, such as a bronze certification, silver certification, or gold certification. Some certifications may allow for a few alert triggers, such as a certification that is issued when the number of alerts has stayed below a threshold number during a threshold period of time (i.e. less than 5 alerts all month long), or a certification that is issued when any alert is handled within a threshold period of time during a threshold period of time (i.e. all alerts handled under 2 hours in all year long).

In some embodiments, certification module 280 issues the certification when an alert fails to trigger within a preconfigured threshold time period. The preconfigured threshold time period may be calculated as a function of information stored in database module 230, such as past performance (e.g., most number of days without an alert) or could be defined via user interface 260. One or more threshold time periods could be defined, allowing for a plurality of certifications. For example, an area without any triggered alerts for 2 days straight could be issued a "good" certification whereas an area without any triggered alerts for 1 week straight could be issued an "excellent" certification. Other certification methods are contemplated, such as defining a certification as being dependent upon the longest time an alert has gone uncorrected within the last week, or as being dependent upon the number of repeated alerts.

Figures 7, 8:
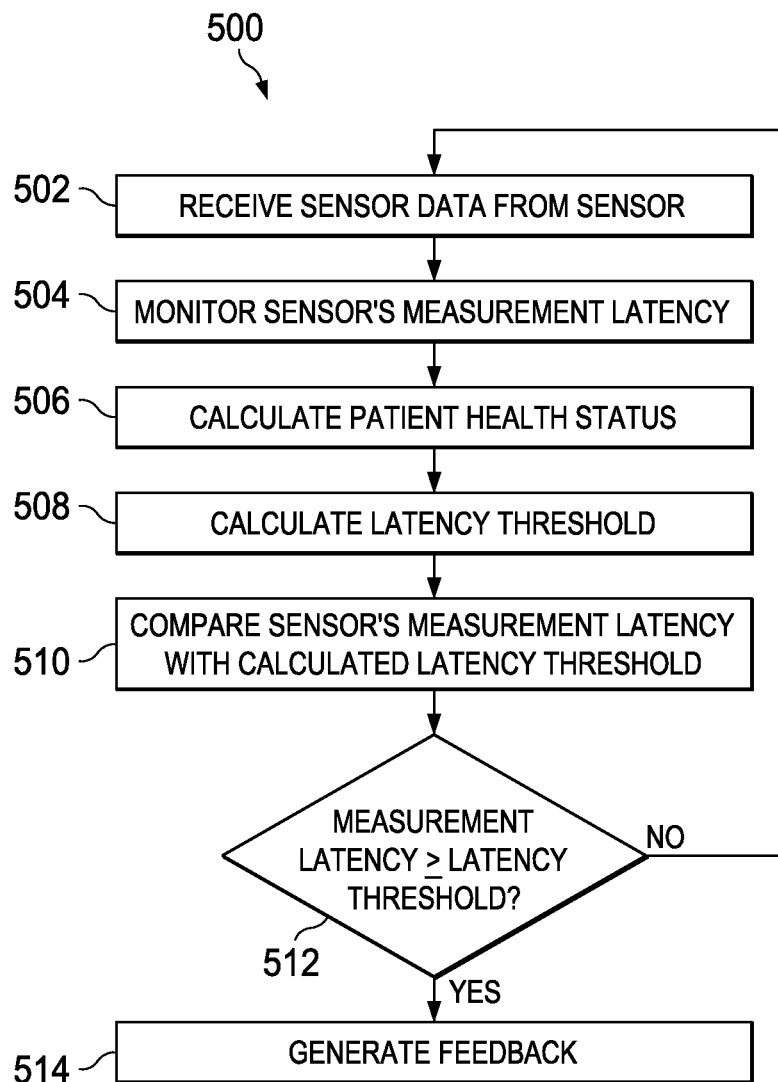
FIG. 7 is a simplified diagram illustrating example details of the system according to an embodiment.
FIG. 8 is a simplified flow diagram illustrating example operations that may be associated with an embodiment of the system.

Turning to FIG. 7, FIG. 7 is a simplified diagram showing a table 300 having an example user interface that shows the status of a real-time monitoring system. Table 300 shows 4 sensors, the value that is gleaned from each sensor, the latency of each sensor (i.e. time that has elapsed since the last sensor collection period), whether an alert has been triggered for each sensor, and a level of certification for each sensor.

Turning to FIG. 8, FIG. 8 is a simplified flow diagram illustrating example operations 500 that may be associated with an embodiment of system 10. At 502, adapter 16 may receive sensor data 14 from sensor 12. At 504, timer 24 may monitor sensor's measurement latency 62. At 506, latency calculator 20 may calculate the patient's health status, for example, based on patient health status factors 46. At 508, latency calculator 20 may calculate latency threshold 22. At 510, comparator 26 may compare sensor's measurement latency 62 with calculated latency threshold 22. At 512, a determination may be made whether sensor's measurement latency 62 is greater than or equal to latency threshold 22. If sensor's measurement latency 62 is less than latency threshold 22, the operations may revert to 502. On the other hand, if sensor's measurement latency 62 is greater than or equal to latency threshold 22, at 514, feedback 64 may be generated. In some embodiments, feedback 64 may comprise an alert. In other embodiments, feedback 64 may comprise an instruction to sensor 12 to change its measurement latency. Various other feedback actions are also possible within the broad scope of the embodiments.

It should be apparent to those skilled in the art that many more modifications besides those already described are possible without departing from the inventive concepts disclosed herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The foregoing discussion provides many example embodiments of systems and methods for alarm fatigue management. Although each embodiment represents a single combination of various elements, all possible combinations of the disclosed elements are intended to be included in the broad scope of the disclosure. Thus if one embodiment comprises elements A, B, and C, and a second embodiment comprises elements B and D, then the scope of the disclosure is considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. Note that any recitation of ranges of values herein is merely intended to serve as a shorthand method of referring individually to each separate value falling within the range. Unless otherwise indicated herein, each individual value is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

[Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. The use of any and all examples, or exemplary language (e.g. "such as") provided with respect to certain embodiments herein is intended merely to better illuminate the invention and does not pose a limitation on the scope of the embodiments otherwise claimed. No language in the specification should be construed as indicating any non-claimed essential.

In example implementations, at least some portions of the activities outlined herein may be implemented in software in, for example, alarm management engine 12. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, adapter 16 and various other components described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc. Moreover, all methods described herein can be performed in any suitable order unless otherwise indicated herein or otherwise clearly contradicted by context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory element 36, database 38) can store data used for the operations described herein. This includes the memory element being able to store instructions (e.g., software, logic, code, etc.) in non-transitory media such that the instructions are executed to carry out the activities described in this Specification. These devices may further keep information in any suitable type of non-transitory storage medium (e.g., random access memory (RAM), read only memory (ROM), field programmable gate array (FPGA), erasable programmable read only memory (EPROM), EEPROM, etc., software, hardware, or in any other suitable component, device, element, or object where appropriate and based on particular needs.

A processor can execute any type of instructions associated with the data to achieve the operations detailed herein in this Specification. In one example, processors (e.g., processor 34) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The information being tracked, sent, received, or stored in system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Note also that the disclosed subject matter herein enables construction or configuration of an adapter to operate on digital data (e.g., raw sensor data, alarm condition, etc.), beyond the capabilities of a human or un-configured (e.g., off-the-shelf) medical device. Although the digital data represents sensor data, it should be appreciated that the digital data is a representation of one or more digital models of a patient's medical measurements (and other indicators) and not the measurements (or indicators) themselves, which comprise activities or operations performed by sensors and/or adapters. By instantiation of such digital models in the memory of the adapter, the adapter is able to manage the digital models in a manner that could provide utility to an individual (e.g., a user of the system) that the individual would lack without such a tool.

It should also be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, random access memory (RAM), flash memory, read-only memory (ROM), etc.). The software instructions can configure a suitable computing device to provide the roles, responsibilities, or other functionality as discussed herein with respect to the disclosed apparatus. In some embodiments, the various servers, systems, databases, or interfaces exchange data using standardized protocols or algorithms, possibly based on hyper-text transfer protocol (HTTP), hyper-text transfer protocol secure (HTTPS), Advanced Encryption Standard (AES), public-private key exchanges, web service application programming interfaces (API's), known financial transaction protocols, or other electronic information exchanging methods. Data exchanges preferably are conducted over a packet-switched network, the Internet, local area network (LAN), wide area network (WAN), virtual private network (VPN), or other type of packet switched network.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting health-care data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 10 may be applicable to other exchanges or routing protocols. Moreover, although system 10 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) or (f) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method for monitoring of a patient, the method comprising:
 monitoring a time delay between successive measurements taken by a sensor connected with the patient;
 determining a time delay threshold based on a health condition of the patient;
 comparing the time delay with the time delay threshold; and generating an alarm based on the comparison indicating that the time delay exceeds the time delay threshold, said alarm indicating that the time delay is not suitable for the health condition of the patient.

2. The method of claim 1, wherein the sensor comprises one or more of a GPS locator, a pulse monitor, a blood pressure monitor, a pulse oximeter, a galvanometer, a blood glucose monitor, a body temperature monitor, or a catheter monitor.

3. The method of claim 1, wherein the sensor is configured to generate sensor data comprising one or more of location information, pulse information, blood pressure information, blood chemical concentration level information, body temperature information, respiration level information, or fluid level information.

4. The method of claim 1, further comprising determining the health condition of the patient based on one or more health condition factors.

5. The method of claim 4, wherein the one or more health condition factors comprise one or more of a location of the patient, a disease of the patient, a health condition of the patient, a location of a physician, clinical pathways associated with the patient, a treatment regimen of a patient, genomic health indicators of a patient, demographic information of the patient, or contextual information of the patient.

6. The method of claim 1, further comprising: sending the alarm to one or more locations.

7. The method of claim 1, further comprising: changing the time delay of the sensor based on the comparison.

8. An apparatus for monitoring a patient, the apparatus comprising:
one or more hardware processors configured to:
monitor a time delay between successive measurements taken by a sensor connected with the patient;
determine a time delay threshold based on a health condition of the patient;
compare the time delay with the time delay threshold; and
generate an alarm based on the comparison indicating that the time delay exceeds the time delay threshold, said alarm indicating that the time delay is not suitable for the health condition of the patient.

9. The apparatus of claim 8, wherein the apparatus comprises an adapter comprising the one or more hardware processors.

10. The apparatus of claim 9, wherein the adapter is configured to be removably attached to the sensor.

11. The apparatus of claim 9, wherein the adapter is integrated with the sensor.

12. The apparatus of claim 9, wherein the adapter is configured to wirelessly communicate with the sensor.

13. The apparatus of claim 8, wherein the one or more hardware processors are further configured to send the alarm to one or more locations.

14. The apparatus of claim 8, wherein the one or more hardware processors are further configured to change the time delay of the sensor based on the comparison.

15. A system for monitoring a patient, the system comprising:
at least one sensor connected with the patient;
a computer system communicatively coupled with the at least one sensor, the computer system comprising one or more hardware processors configured to:
monitor a time delay between successive measurements taken by the at least one sensor connected with the patient;
determine a time delay threshold based on a health condition of the patient;
compare the time delay with the time delay threshold; and
generate an alarm based on the comparison indicating that the time delay exceeds the time delay threshold, said alarm indicating that the time delay is not suitable for the health condition of the patient.

16. The system of claim 15, wherein the at least one sensor comprises one or more of a GPS locator, a pulse monitor, a blood pressure monitor, a pulse oximeter, a galvanometer, a blood glucose monitor, a body temperature monitor, or a catheter monitor.

17. The system of claim 15, wherein the at least one sensor is configured to generate sensor data comprising one or more of location information, pulse information, blood pressure information, blood chemical concentration level information, body temperature information, respiration level information, or fluid level information.

18. The system of claim 15, further comprising a network over which the computer system communicates with the at least one sensor.

19. The system of claim 15, wherein the at least one sensor comprises a first sensor, a second sensor, and a third sensor.

20. The system of claim 19, wherein the one or more hardware processors are further configured to change the time delays of the second and third sensors in response to the alarm based on the first sensor.

* * * * *